United States Patent [19]

Johnson

[11] 4,015,336
[45] Apr. 5, 1977

[54] VALVE FOR AN ORAL EVACUATOR SYSTEM

[76] Inventor: W. Grant Johnson, 717 E. Chapman, Orange, Calif. 02007

[22] Filed: July 1, 1975

[21] Appl. No.: 592,140

[52] U.S. Cl. .................................. 32/33; 128/276; 251/347; 251/348

[51] Int. Cl.² .......................................... A61C 17/04

[58] Field of Search .......... 251/347, 348, 321, 340, 251/341, 343, 337, 318, 63.4, 294; 128/274, 276; 32/33; 222/518

[56] References Cited

UNITED STATES PATENTS

| 697,109 | 4/1902 | Strong | 291/348 |
|---|---|---|---|
| 2,163,925 | 6/1939 | Wagner | 251/318 |
| 2,208,031 | 7/1940 | Hooper | 251/321 |
| 3,015,469 | 1/1962 | Falk | 251/294 |
| 3,071,402 | 1/1963 | Lasto et al. | 128/276 |
| 3,146,987 | 9/1964 | Krayl | 128/276 |
| 3,645,497 | 2/1972 | Nyboer | 32/33 |

Primary Examiner—William R. Cline
Assistant Examiner—H. Jay Spiegel
Attorney, Agent, or Firm—Albert H. Graddis; Jeremiah J. Duggan

[57] ABSTRACT

A specific embodiment provides a valve structure for an oral evacuator system adapted to be connected to a source of negative pressure. The valve structure includes an elongated housing having a longitudinal bore extending through the housing, a valve seat formed by a reduced diameter portion of the bore, and a slot extending through the housing to the bore and longitudinally of the housing. A valve member is situated in the bore for abutting engagement with the valve seat to prevent passage of flowable materials therebetween. A spring is provided for biasing the valve member into abutting engagement with the valve seat, and the spring includes an offset portion extending outwardly through the slot. A manually operable member is connected to the offset spring portion for moving the offset spring portion to compress the spring and thereby move the valve member out of engagement with the valve seat to permit passage of flowable materials therebetween.

7 Claims, 7 Drawing Figures

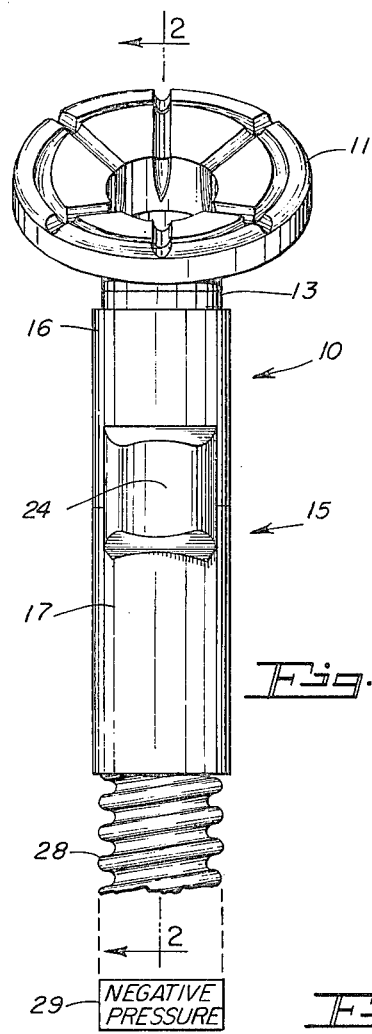
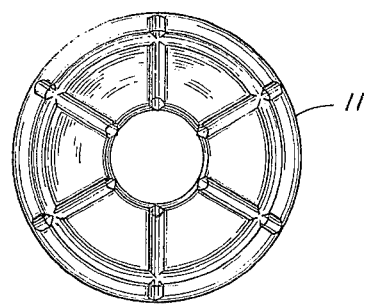
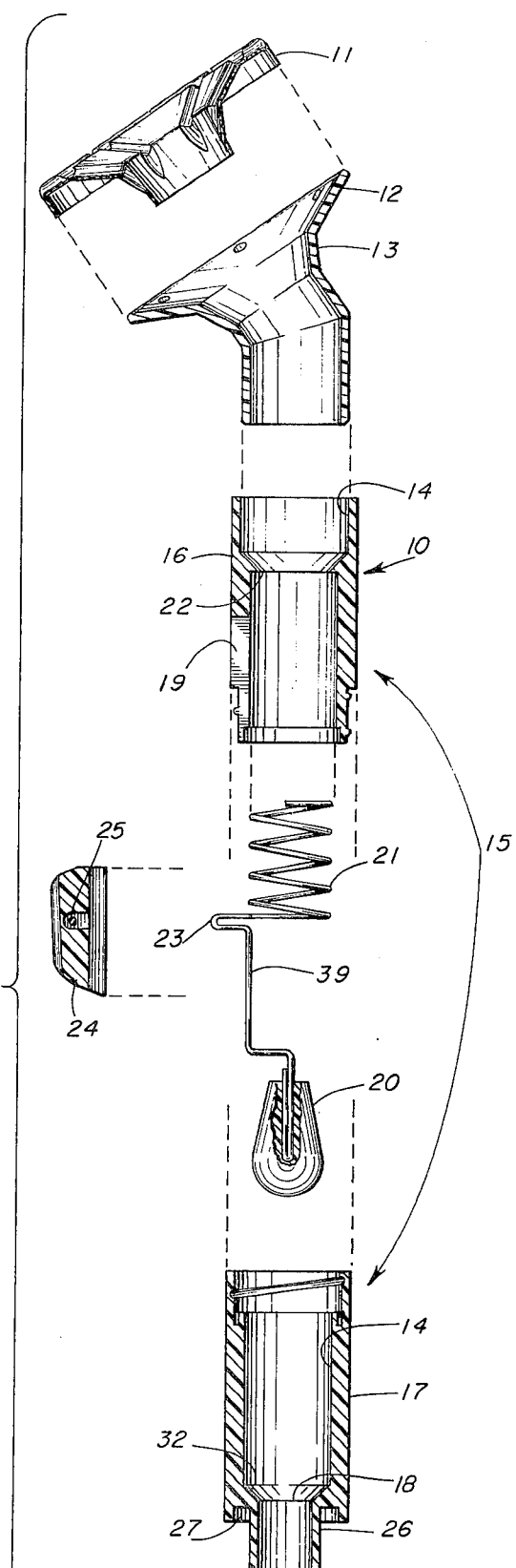

VALVE FOR AN ORAL EVACUATOR SYSTEM

BACKGROUND OF THE INVENTION

The present invention relates to a valve structure for an oral evacuator system useful in dentistry. More specifically, the present invention relates to a valve structure located in the hand-held portion of an evacuator system which is operable between opened and closed positions by either the patient or the dentist.

While being treated by a dentist, a patient is frequently required to lean from the dental chair to rinse his mouth. U.S. Pat. No. 3,742,607 discloses an oral evacuator system which provides a hand-held assembly connected to a vacuum source which is brought to the mouth of a patient to cleanse rinsing water and other flowable materials therefrom.

SUMMARY OF THE INVENTION

The present invention provides a valve structure for an oral evacuator system such as disclosed in U.S. Pat. No. 3,742,607. In accordance with the present invention there is provided a valve structure for an oral evacuator system adapted to be connected to a source of negative pressure. The valve structure includes an elongated housing having a longitudinal bore extending through the housing, a valve seat formed by a reduced diameter portion of the bore, and a slot extending through the housing to the bore and longitudinally of the housing. A valve member is situated in the bore for abutting engagement with the valve seat to prevent passage of flowable materials therebetween. A spring is provided for biasing the valve member into abutting engagement with the valve seat, and the spring includes an offset portion extending outwardly through the slot. A manually operable member is connected to the offset spring portion for moving the offset spring portion to compress the spring and thereby move the valve member out of engagement with the valve seat to permit passage of flowable materials therebetween.

BRIEF DESCRIPTION OF THE DRAWINGS

FIG. 1 is a front elevational view of a hand-held portion of an oral evacuator system incorporating an embodiment of the present invention;

FIG. 2 is an exploded cross-sectional view taken along lines 2—2 of FIG. 1 showing the components of an embodiment of the present invention;

FIG. 3 is a top plan view of a replaceable and disposable mouthpiece of the hand-held portion of the system shown in FIG. 1;

DESCRIPTION OF SPECIFIC EMBODIMENTS

Figure 4:
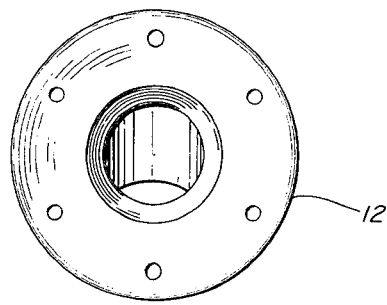
FIG. 4 is a top plan view of a removable head of the hand-held portion shown in FIG. 1.
Figure 5:
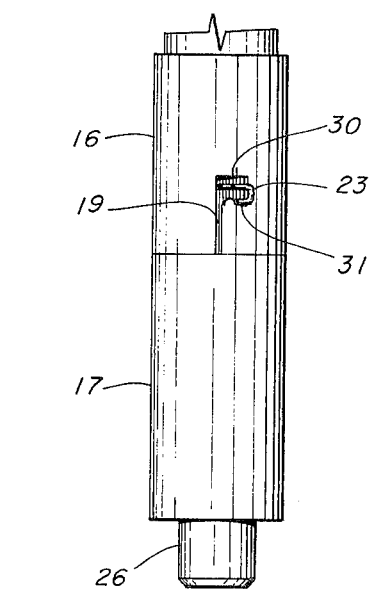
FIG. 5 is a side elevational view of a portion of FIG. 1 with a finger operable member removed.

With reference to FIGS. 1–6, a hand-held 10 of an oral evacuator system has a replaceable mouthpiece 11 at the upper end thereof. The mouthpiece 11 is fitted about an outwardly flared end 12 of a head member 13. The head member 13 is frictionally seated in the upper portion of a bore 14 formed in a housing 15. The housing 15 has an upper member 16 threaded at the lower end thereof for threading engagement with a lower member 17.

A valve seat 18 is formed in the lower member 17 of the housing 15 by a reduced diameter portion of the bore 14. A valve member 20 is positioned in the bore 14 in abutting engagement with the valve seat 18, and a spring 21 is connected to the valve member 20 at the lower end thereof and in abutting engagement with a shoulder 22 formed in a bore 14 to bias the valve member 20 into an abutting engagement with the valve seat 18.

The spring 21 has an offset looped portion 23 extending outwardly through a slot 19 in the upper member 16. A finger engageable member 24 is connected to the offset looped portion 23 by a pin 25 extending transversely through the finger operable member 25 and beneath the looped portion 23.

The bottom of the lower member 17 has a reduced diameter portion 26 extending outwardly from annulus 27. The reduced diameter portion 26 is fitted into a flexible hose 28 which is seated in the annulus 27. The downstream end of the housing 15 is connected to a source of negative pressure 29. The negative pressure source 29 must be of sufficient vacuum to draw flowable materials from the mouth of a patient into the head 13, and through the bore 14 and between the valve member 20 and valve seat 18 to the interior of the hose 28. For example, the negative pressure may be a vacuum in the order of 4 to 6 p.s.i. less than atmospheric pressure.

Figure 6:
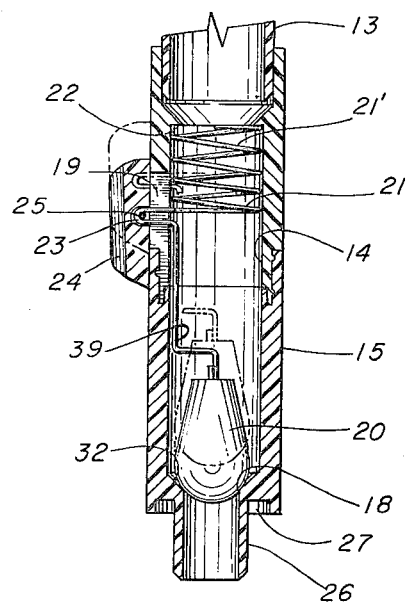
FIG. 6 is a cross-sectional view of the valve structure embodiment of FIG. 2 with the components assembled.

The manually operable member 24 and offset spring portion 23 are movable upwardly in the slot 19 to the position shown in dashed lines in FIG. 6 to compress spiral portion of the spring 21 and lift the valve member 20 upstream out of engagement with the valve seat 18. The patient or dentist may hold the manually operable member 24 in this position to evacuate flowable materials from the patient's mouth. Alternatively, the valve structure can be locked in an opened position by positioning the offset portion 23 in a transverse portion 30 (FIG. 5) of the slot 19. The transverse slot portion 30 extends downwardly a slight distance at 31 (FIG. 5) to seat the offset portion 23 therein. Thus, to close the valve assembly, the manually operable member 24 is first moved upwardly to lift the offset portion 23 out of seating engagement in the transverse slot portion 30. Then, the manually operable member is moved transversely to the left, as viewed in FIG. 5, to position the offset portion 30 in the longitudinal position of the slot 19. Thereafter, the bias of the spring 21 moves the valve member 20 into seating engagement with the valve seat 18 to prevent passage of flowable materials therebetween. The bore 14 is beveled 32 to guide the valve member 20 into the engagement with the valve seat 18.

The manually operable member 24 is dimensioned to cover the slot 19, including the transverse slot portion 23, irrespective of the position of the offset spring portion 23 in the slot 19. By covering the slot 19 throughout operation of the valve structure, the loss of negative pressure at the slot 19 is reduced or immunized.

In the embodiment shown in FIGS. 2 and 6, the offset spring portion 23 is formed between the spiral portion 21 upstream of the valve member 20 and the extension 39 of the spring 21 that is connected to the valve member 20. By positioning the spring 21 and the valve member 20 upstream of the valve seat 18, the negative pressure source 29 aids the spring 21 in maintaining the valve member 20 in abutting egagement with the valve seat.

Obviously, the valve member 20 and the spring 21 may be situated downstream of the valve seat 18, but, in this case, the negative pressure source 29 would pull against the bias of the spring 21 to tend to move the valve member 20 out of engagement with the valve seat 18.

Figure 7:
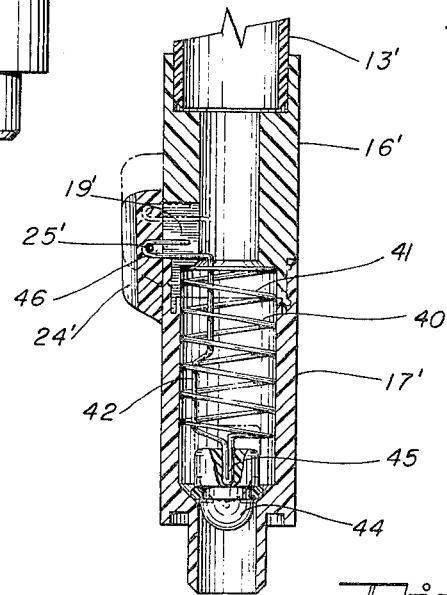
FIG. 7 is a cross-sectional view of another valve structure embodiment in accordance with the present invention.

In an alternative embodiment shown in FIG. 7, the spring 40 has an extension 42 connected at 45 to the valve member 44 downstream of the spiral portion 41. The extension 42 is folded back through the spiral portion 41, and the offset spring portion 46 is at the upper end of the extension 42 upstream of the spiral portion 41. As in the embodiment of FIGS. 2 and 6, the offset spring portion 46 extends through the slot 19' in the upper member 16' and is connected to the manual or finger-operable member 24' by the pin 25'.

What is claimed is:

1. A valve structure for an oral evacuator system adapted to be connected to a source of negative pressure, said valve structure comprising:
   a member adapted for contact with the mouth;
   an elongated housing including a lingitudinal bore extending through said housing connecting to said member at its distal end and adapted to connect to source of negative pressure at its proximal end, having a valve seat formed by a reduced diameter portion of said bore, and a slot extending through said housing to said bore and lonitudinally of said housing;
   a valve member moveable distally of said source of negative pressure in said bore for abutting engagement with said valve seat to prevent passage of flowable materials therebetween;
   a spring connected to said housing and to said valve member for biasing said valve member into abutting engagement with said valve seat, said spring including an offset portion extending outwardly through said slot; and
   a manually operable member exteriorly of said housing and connected to said offset spring portion remotely of said valve member for moving said offset spring portion in said slot and compressing said spring, whereby said valve member moves out of engagement with said valve seat to permit passage of flowable materials therebetween, said operable member being adapted to substantially seal said slot when said spring is compressed.

2. The valve structure of claim 1, wherein said bore includes a beveled portion for guiding said valve member into abutting engagement with said valve seat.

3. The valve structure of claim 1 wherein said slot includes a transverse portion, and wherein said valve member is locked out of engagement with said valve seat by positioning said offset spring portion in said transverse slot portion.

4. The valve structure of claim 1 wherein manually operable member is dimensioned to cover said slot irrespective of the position of said offset spring portion in said slot.

5. The valve structure of claim 1 wherein said spring has a spiral portion, and wherein said offset spring portion is formed in an extension of one end of said spiral portion.

6. The valve structure of claim 5 wherein said extension is connected to said valve member downstream of said spiral portion, and wherein said offset spring portion is formed between said spiral portion and said valve member.

7. The valve structure of claim 5 wherein said extension is connected to said valve member downstream of said spiral portion, and is folded back through said spiral portion, and wherein said offset spring portion is formed upstream of said spiral portion.

* * * * *

UNITED STATES PATENT OFFICE
CERTIFICATE OF CORRECTION

PATENT NO. : 4,015,336
DATED : April 5, 1977
INVENTOR(S) : W. GRANT JOHNSON

It is certified that error appears in the above-identified patent and that said Letters Patent are hereby corrected as shown below:

Column 1, line 64, after "hand-held", insert --portion--.

Signed and Sealed this

Eleventh Day of April 1978

[SEAL]

Attest:

RUTH C. MASON
Attesting Officer

LUTRELLE F. PARKER
Acting Commissioner of Patents and Trademarks